(12) United States Patent
Alburty et al.

(10) Patent No.: US 10,953,350 B2
(45) Date of Patent: Mar. 23, 2021

(54) DEVICES, SYSTEMS, AND METHODS FOR REMOVAL OF SOLUBLE GASES FROM FLUID SAMPLES

(71) Applicant: InnovaPrep LLC, Drexel, MO (US)

(72) Inventors: David Scott Alburty, Drexel, MO (US); Michael Lee Hornback, Olathe, KS (US); Bryan Charles Long, Odessa, MO (US); Andrew Edward Page, Smithton, MO (US)

(73) Assignee: INNOVAPREP, LLC, Drexel, MO (US)

( * ) Notice: Subject to any disclaimer, the term of this patent is extended or adjusted under 35 U.S.C. 154(b) by 144 days.

(21) Appl. No.: 15/960,483

(22) Filed: Apr. 23, 2018

(65) Prior Publication Data

US 2018/0304176 A1 Oct. 25, 2018

Related U.S. Application Data

(60) Provisional application No. 62/488,693, filed on Apr. 21, 2017.

(51) Int. Cl.
| | |
|---|---|
| *A47G 19/22* | (2006.01) |
| *B01D 19/00* | (2006.01) |
| *G01N 1/40* | (2006.01) |
| *G01N 1/42* | (2006.01) |
| *C12H 1/18* | (2006.01) |
| *A23L 5/20* | (2016.01) |
| *G01N 33/14* | (2006.01) |

(52) U.S. Cl.
CPC ............ *B01D 19/0073* (2013.01); *A23L 5/21* (2016.08); *A47G 19/22* (2013.01); *A47G 19/2233* (2013.01); *B01D 19/00* (2013.01); *C12H 1/18* (2013.01); *G01N 1/4005* (2013.01); *G01N 1/4055* (2013.01); *G01N 1/42* (2013.01); *G01N 33/146* (2013.01); *A23V 2002/00* (2013.01)

(58) Field of Classification Search
CPC ..... A47G 19/22; A47G 19/2233; B01D 19/00
See application file for complete search history.

(56) References Cited

U.S. PATENT DOCUMENTS

| | | | | |
|---|---|---|---|---|
| 4,322,008 | A * | 3/1982 | Schneider | .......... A47G 19/2233 215/371 |
| 10,477,997 | B1 * | 11/2019 | Bunkers | ............. A47G 19/2233 |

OTHER PUBLICATIONS

International Search Report and Written Opinion; International Application No. PCT/US18/28965; dated Jul. 17, 2018.

* cited by examiner

*Primary Examiner* — Robert A Hopkins
(74) *Attorney, Agent, or Firm* — Moazzam & Associates, LLC

(57) ABSTRACT

Devices, systems and methods are disclosed which relate to using containers with a multitude of nucleation sites covering a major portion of the inside wall of the container to enable rapid and nearly complete removal of soluble gases from fluid samples, including carbonated beverages and other carbonated fluid samples. A fluid sample is rapidly poured into the described container initiating a catastrophic release of the soluble gas from the sample.

17 Claims, 10 Drawing Sheets

DEVICES, SYSTEMS, AND METHODS FOR REMOVAL OF SOLUBLE GASES FROM FLUID SAMPLES

This application claims priority to U.S. Provisional Patent Application Ser. No. 62/488,693, filed on Apr. 21, 2017, the contents of which are hereby incorporated by reference herein in their entirety into this disclosure.

TECHNICAL FIELD

The present subject disclosure relates generally to the fields of beverage quality control, food safety, and other applications where efficient removal of carbon dioxide from beverages or other aqueous samples is desirable prior to performing analytical methods, including methods for concentration and detection of spoilage organisms and other microorganisms in carbonated beverages.

BACKGROUND OF THE SUBJECT DISCLOSURE

Spoilage organisms can grow in carbonated beverages, such as widely produced beers, ales, and soft drinks. These organisms, while typically initially present only at very low concentrations, can reproduce over time, producing off-flavors, increased turbidity, and other quality defects. Further, in some cases these organisms can create safety concerns due to the potential for increased carbon dioxide pressure and risk of bursting bottles.

Current methods for detection of these organisms are time-consuming and tedious, can impact the viability of entrained contaminant organisms, and are difficult to perform in an aseptic manner—thus increasing the potential for producing erroneous results due to introduced contaminates. Established methods include, but are not limited to, ultrasonication, filtration, combinations of ultrasonication and filtration, automated rotary shakers, compressed air sparging (purging), and manual degassing by pouring back and forth (Smith & Marinelli, 1991). The American Society of Brewing Chemists (ASBC) compared ASBC Method Beer-1A (shaking in a flask until no further gas escapes) with gas purging, mechanical shakers, gas-permeable membrane techniques, ultrasonication, and bench-top rotary shakers (Constant & Collier, 2017). The bench-top rotary shaker with baffled Erlenmeyer flasks was determined to be the preferred method.

There is a great economic need for rapid identification of spoilage organisms in carbonated beverages; both to reduce hold times prior to release of product and to reduce the possibility of damage to the reputation and brand of the producer. Current methods of determining the presence of contaminating microorganisms involves plating on Petri dishes for identification and enumeration, or other methods of classical microbiology. Rapid methods for microbiological analysis (RMMs) such as polymerase chain reaction (PCR), immunoassays, and flow cytometry are becoming widespread. However, use of RMMs is limited in their application to the beverage industry due to the very small volume processed; typically 5 to 1000 microliters. This small volume is not adequately representative of the volume of fluid in even one single beverage container, which is typically 200 to 1000 milliliters, up to a thousand-fold greater volume than the amount analyzed.

Various conventional methods of decarbonation of beer are briefly described below.

Shaking for Decarbonation: One published method of decarbonation of beer samples involves placing a beer sample into a large Erlenmeyer flask and shaking gently at first and then vigorously. While this method removes carbon dioxide and is relatively simple, it is difficult to implement in large laboratories performing analysis of many samples. According to Paul Smith et. al., the required analyst time for preparing 10 samples using this method is 25 minutes and it requires significant space due to the large size of the flasks (500 mL flask for 200 mL of beer). See Smith, P. and Marinelli, L., Evaluation of Established Methods of Decarbonating Beer. ASBC Journal. Mar. 27, 1992.

Pouring for Decarbonation: Another method for decarbonation entails pouring beer samples back and forth between beakers. This method removes carbon dioxide but is similar to the shaking method discussed above in terms of labor requirements—also requiring 25 minutes to prepare 10 samples. Further, this method is inherently not aseptic due to the significant number of times that the sample must be poured, and thus is not a good method for use prior to spoilage organism testing.

Filtration for Decarbonation: In some instances, filtration of beer samples has been used to remove carbon dioxide. Movement of the sample from atmospheric pressure through a small pore and into a low pressure environment causes carbon dioxide to be released both on the retentate and the permeate sides of the filter. It is inherent in this process that smaller pore sizes cause release of greater quantities of carbon dioxide. This fact, in general, eliminates this method from use as a front end to the Concentrating Pipette and other membrane filtration methods for concentration of microorganisms, due to the need for a very large percentage of the target microorganisms to be present in the sample prior to and after concentration. Use of a pore size large enough to allow larger target microorganisms to pass inherently leaves too much carbon dioxide in the sample, and therefor will not allow sufficient volume to be processed with the Concentrating Pipette.

Ultrasonication for Decarbonation: Ultrasonication is capable by itself or in combination with other methods of removing carbon dioxide from beer samples, but it is generally not readily capable of removing carbon dioxide to the levels necessary prior to processing with the Concentrating Pipette or other membrane filters. Further, ultrasonication is known to have detrimental effects on the viability of certain microorganisms.

Beer Glasses with Nucleation Sites. Beer glasses are now commercially available with laser cut nucleation sites on the inside wall of the bottom of the glass. These nucleation sites are used to enhance aroma, taste and head retention in beer. The nucleation surface area is purposely limited to a very small percentage of the inside glass surface to create a very slow steady release of carbon dioxide in order to create bubbles and maintain a beer head. The nucleated surface area is typically way less than 1% of the surface area, and more often less than 0.1% of the surface area. In this way, only a very small percentage of the contained carbon dioxide is released from the beer.

SUMMARY OF THE SUBJECT DISCLOSURE

The ability to concentrate any organisms present in a significant amount of the beverage will increase the utility of RMMs by increasing the likelihood of early detection, benefiting industry and consumers. Applicant specializes in membrane-based concentration of biological particles from fluids and has been awarded six US patents in this area to-date; U.S. Pat. Nos. 8,110,112, 8,758,623, 8,584,535, 9,593,359, 9,574,977, and 8,726,744, all of which are incorporated by reference herein in their entirety into this disclosure. Three commercial biological concentrators have been developed and sold, based on the patented process, termed "WET FOAM ELUTION", the HSC-40, HCl-40, and CP-150 Concentrating Pipette (current data sheets available at www.innovaprep.com).

As used herein and throughout this disclosure, the Concentrating Pipette is as described in the various patents incorporated by reference in this disclosure. An example of such a Concentrating Pipette Instrument is shown in FIG. 10. One of the advantages of the present subject disclosure is in preparing a sample size from a carbonated fluid to the Concentrating Pipette device.

While Applicant has demonstrated that the concentration of biological particles from a carbonated fluid can be performed using the patented methods and commercial instruments at increased pressure, thus keeping the gas in solution, Applicant's patented method of concentration was not effective for carbonated beverage samples at ambient pressures. A reason for this is because the vacuum applied to the filter releases gas from the fluid as it is drawn through the membrane, blocking the pores in the membrane. The solubility of carbon dioxide in water (and thus an alcoholic beverage, e.g., beer) at various temperatures is significant. FIG. 1 shows high solubility of carbon dioxide in water, particularly at lower temperatures.

In the present subject disclosure, Applicants have demonstrated a novel method for rapid degassing of carbonated beverage samples by pouring them into an etched or "frosted" glass or plastic container with enough volume to hold the sample as it catastrophically foams up, evolves the majority of the carbon dioxide gas, and collapses as flat liquid in the bottom of the container.

This process uses a container that has been treated using sandblasting or other methods to create a multitude of nucleation sites on a large surface area on the inside of the container. By creating nucleation sites over a major portion of the inside area of the container, the nucleation sites not only cause a release of carbon dioxide, but also initiate a catastrophic release of carbon dioxide through formation of a multitude of gas bubbles causing significant mixing and additional release of gas.

This catastrophic release of carbon dioxide is efficient enough that after several minutes of settling, enough carbon dioxide is evolved that the sample is free enough of carbon dioxide to allow for processing through a membrane filter such as those in the Concentrating Pipette Tips used in the Concentrating Pipette instrument.

Further, vigorous pouring of the sample into the container further enhances the catastrophic release of carbon dioxide and further reduces the amount of residual carbon dioxide present. In some instances, the use of a mild heating step prior to pouring into the container can be used to reduce the solubility of carbon dioxide in the sample to further enhance the release of carbon dioxide from the sample. Finally, refrigeration of the sample, immediately after pouring into the decarbonation container or several minutes later, can further enhance the ability to process through membrane filters by increasing the solubility of the carbon dioxide— making it more difficult to remove during the membrane filtration process.

BRIEF DESCRIPTION OF THE DRAWINGS

The accompanying drawings, which are incorporated in and constitute a part of this specification, illustrate embodiments of the subject disclosure and technical data supporting those embodiments, and together with the written description, serve to explain certain principles of the subject disclosure.

DETAILED DESCRIPTION OF THE SUBJECT DISCLOSURE

The following detailed description references specific embodiments of the subject disclosure and accompanying figures, including the respective best modes for carrying out each embodiment. It shall be understood that these illustrations are by way of example and not by way of limitation.

The present subject disclosure describes highly efficient and simple to use devices, systems, and methods for removing saturated gasses, such as carbon dioxide, from liquid samples. The technique uses a large surface area of nucleation sites along with methods for enhancing the nucleation of the gasses to quickly and efficiently remove these gases from samples prior to implementing liquid concentration or other laboratory methods. Specifically, the present technique may be used to decarbonate beer and other carbonated liquids prior to processing on a Concentrating Pipette Instrument, for example those described and patented by the Applicant.

Figure 1:
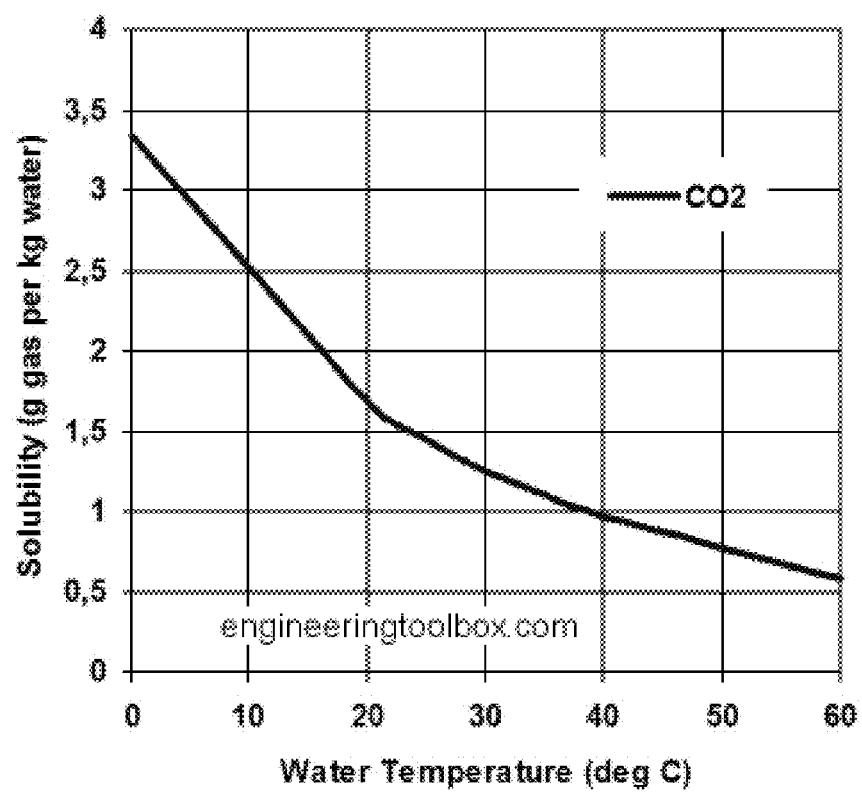
FIG. 1 shows the solubility of carbo dioxide in water.
Figure 2:
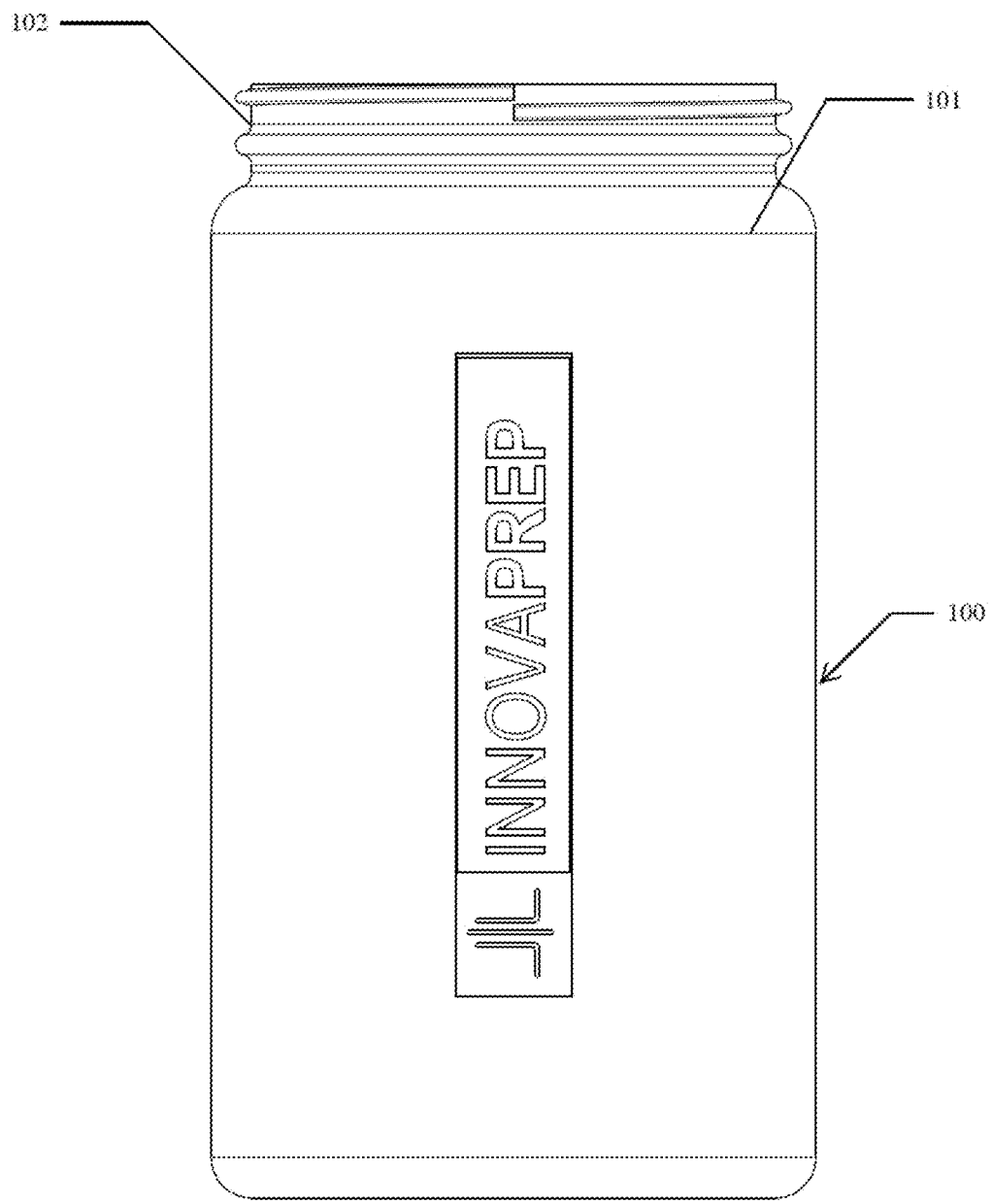
FIG. 2 shows a decarbonation container, according to an exemplary embodiment of the present subject disclosure.

FIG. 2 shows a decarbonation container 100, according to an exemplary embodiment of the present subject disclosure. A large zone of nucleation sites 101, on the inside surface of the container, extends from near the neck at the top end to the bottom edge of the inside walls and includes the entire bottom inside surface as well. Thus, any fluid which is poured into container 100 will come into direct contact with the nucleation sites 101, which extend to nearly the entire interior surface of the container 100. The higher the percentage of inside walls of container 100 is covered by nucleation sites 101, the more effective the decarbonation of a fluid deposited therein. Typically, the nucleated interior surface is 5%-100% of the interior surface. Further, a standard bottle thread 102 is provided to allow for use of a threaded lid.

Figure 3:
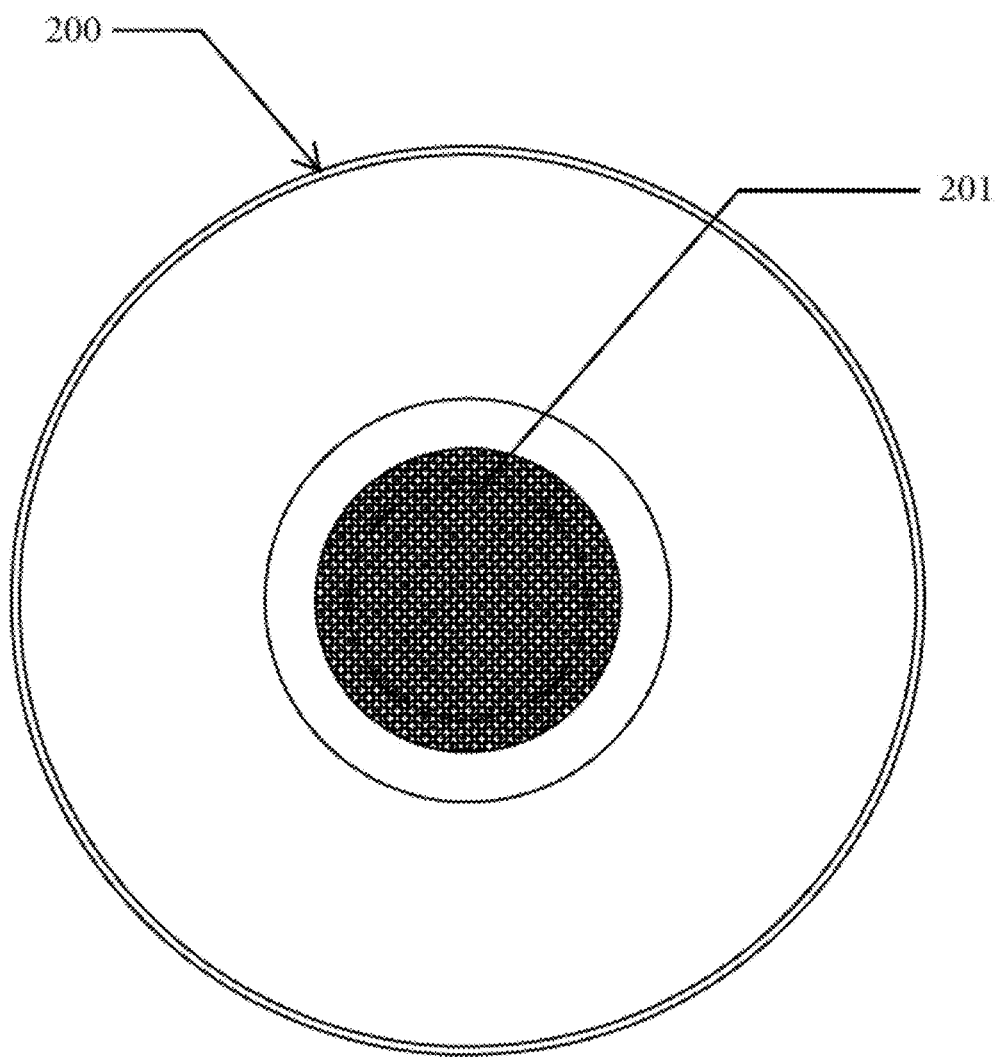
FIG. 3 shows a vented lid for a decarbonation container, according to an exemplary embodiment of the present subject disclosure.

FIG. 3 shows a screw top lid 200 including a hydrophobic membrane filter vent 201 for use on container 100. The user pours a carbonated sample into container 100 and carbon dioxide is nucleated by nucleation surface 101. After pouring the sample into the container 100, the user may place lid 200 onto container 100 to reduce the potential for contamination of the liquid sample. Vent 201 allows gas to escape during the decarbonation process so that pressure does not build up within container 100.

Applicant has demonstrated sufficient rapid degassing of carbonated beverage samples by pouring them into glass or plastic containers that have had a major portion of the inside walls etched or "frosted" and which contain enough volume to hold the sample as it catastrophically foams up, evolving the majority of the carbon dioxide gas, and collapsing as flat liquid in the bottom of the container.

Figure 4:
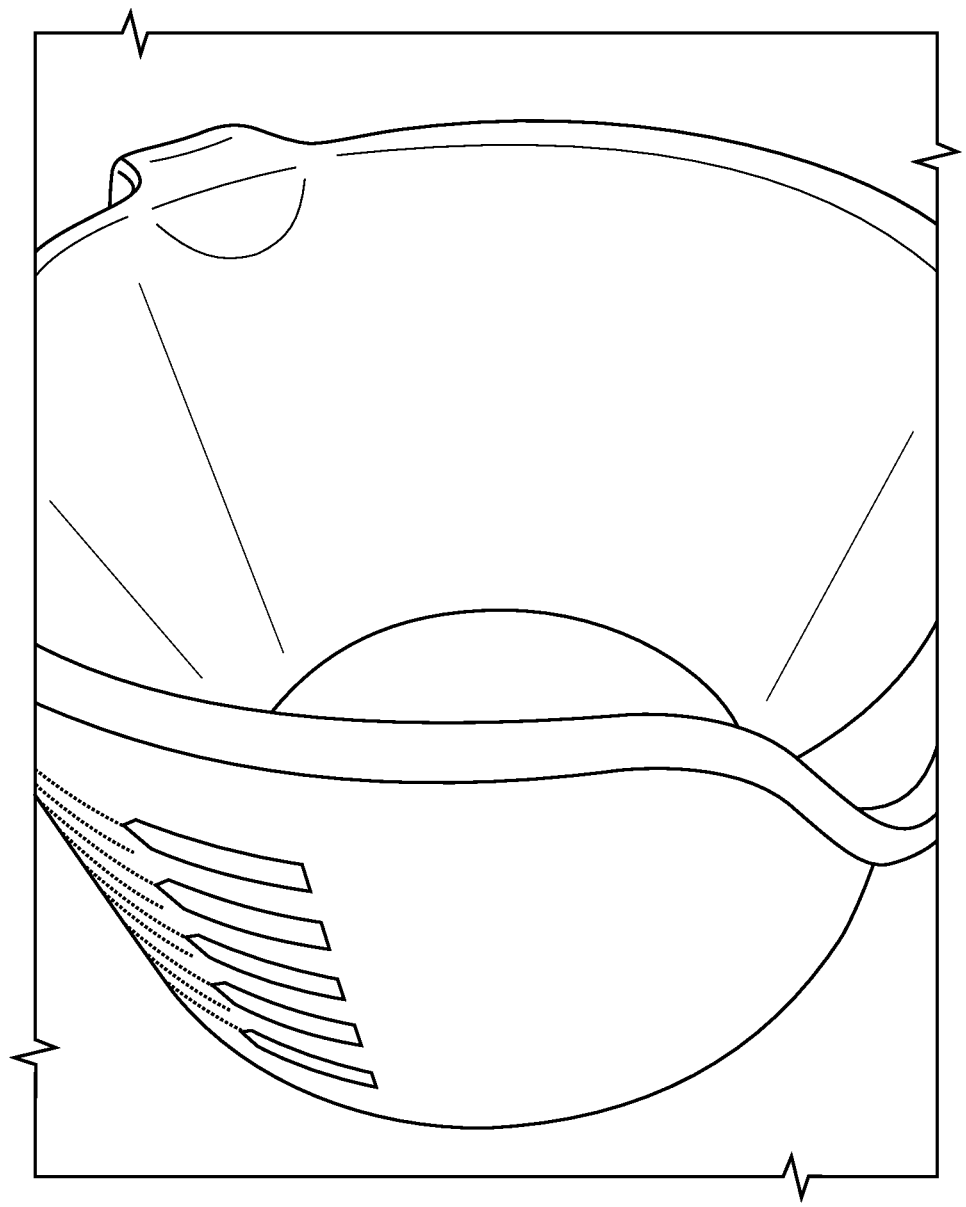
FIG. 4 shows a nucleated PYREX measuring cup, according to an exemplary embodiment of the present subject disclosure.
Figure 5:
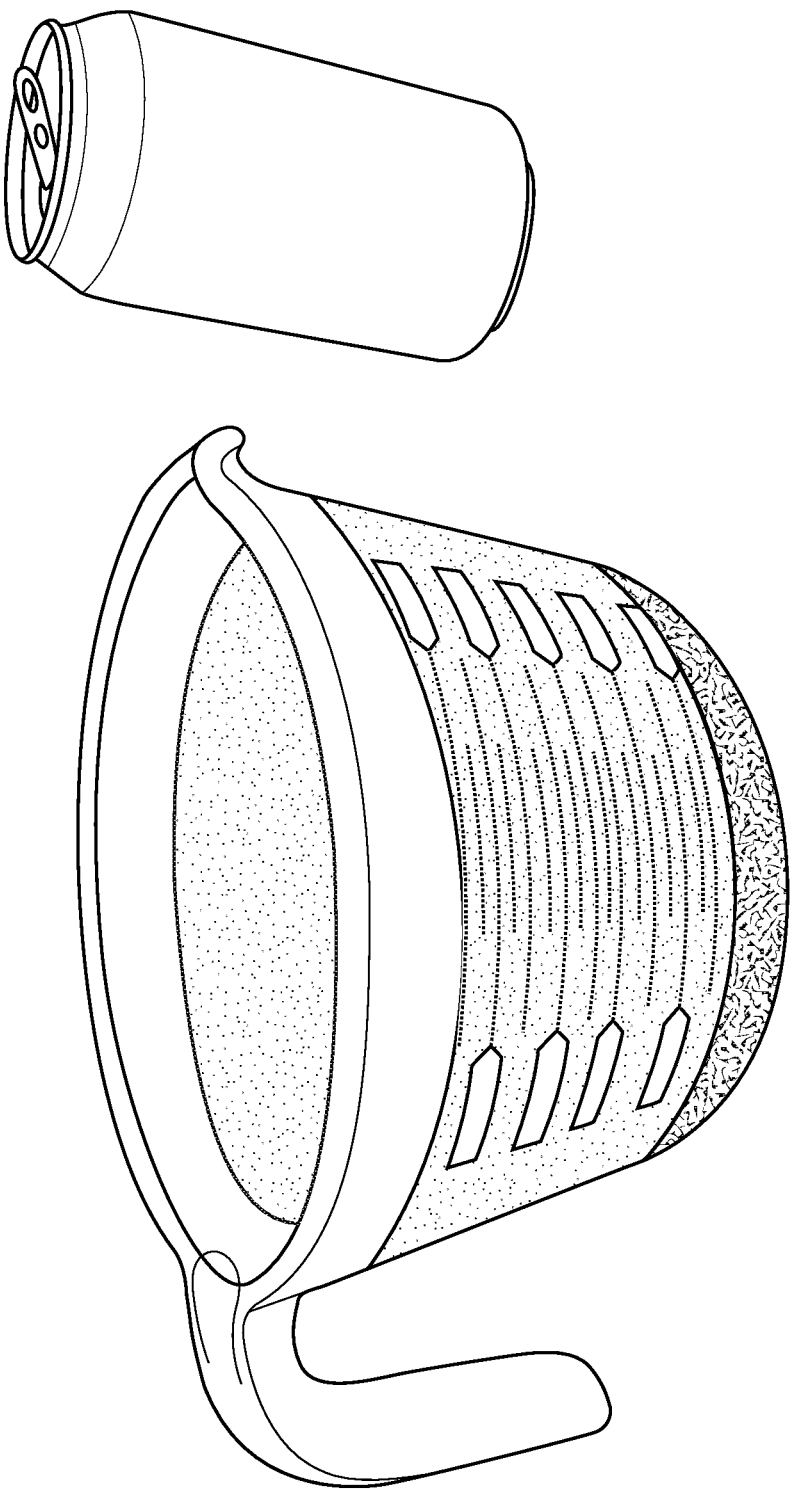
FIG. 5 shows beer poured into a nucleated container, according to an exemplary embodiment of the present subject disclosure.
Figure 6:
FIG. 6 shows flattened beer being concentrated, according to an exemplary embodiment of the present subject disclosure.
Figure 7:
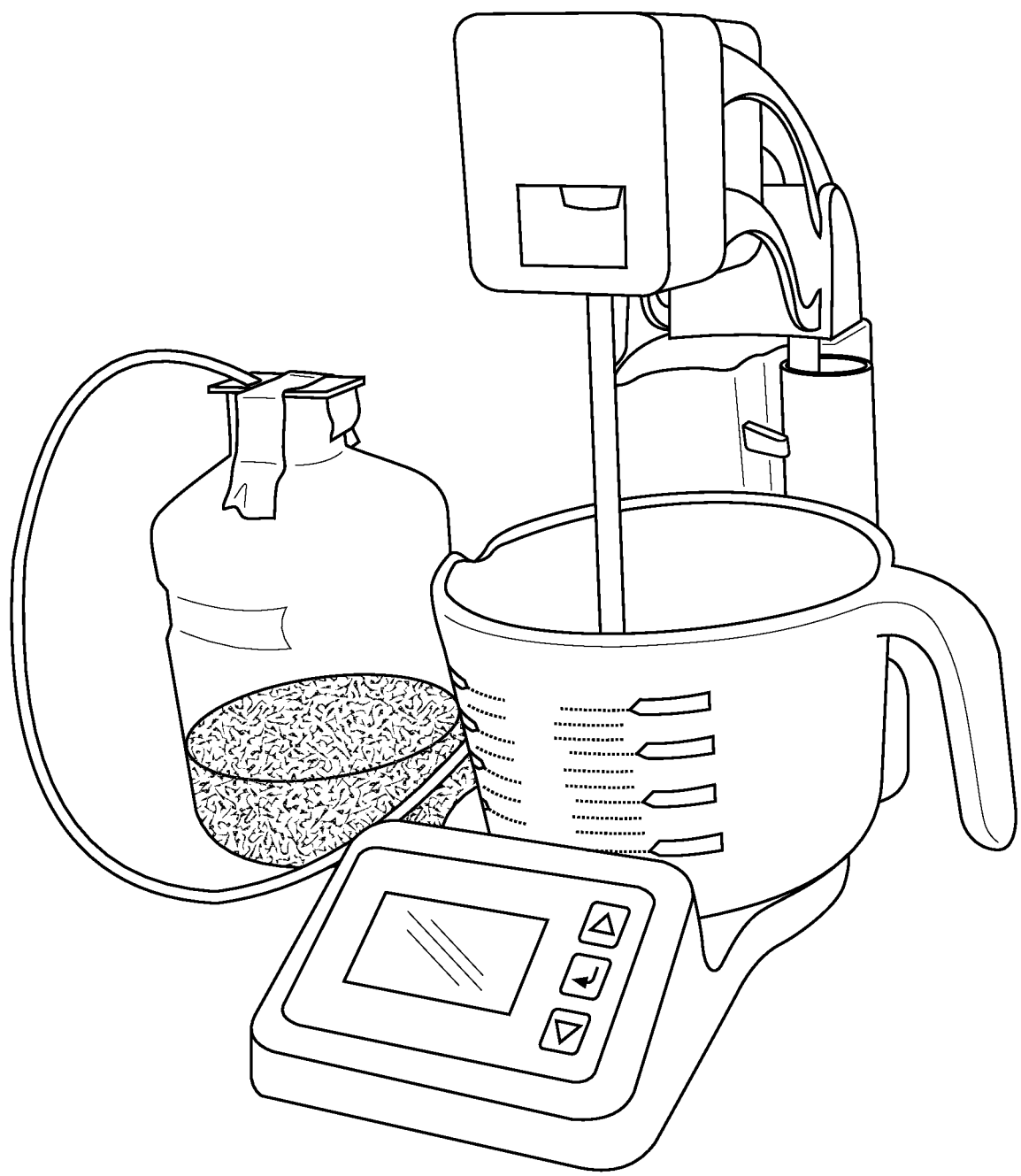
FIG. 7 shows a 12 ounce can of flattened beer filtered, according to an exemplary embodiment of the present subject disclosure.

An exemplary demonstration of the process was accomplished by grit blasting a 2 Liter Pyrex Measuring Cup (see FIG. 4). The blasting process "frosted" the interior of the container, forming nucleation sites over the internal surface. When a can or bottle of beer was poured into the container, it immediately foamed up to the top, then rapidly collapsed back to a flat liquid with very little residual carbonation (FIG. 5). As is shown in FIGS. 6-7, the entire bottle or can is then able to be rapidly processed using the Concentrating Pipette Instrument. In the example shown, the CP-150 Concentrating Pipette Instrument was used. This Instrument is shown again in FIG. 10. As an example, a 12 ounce can of Busch Light beer was filtered in 7 minutes and 43 seconds.

Figure 8:
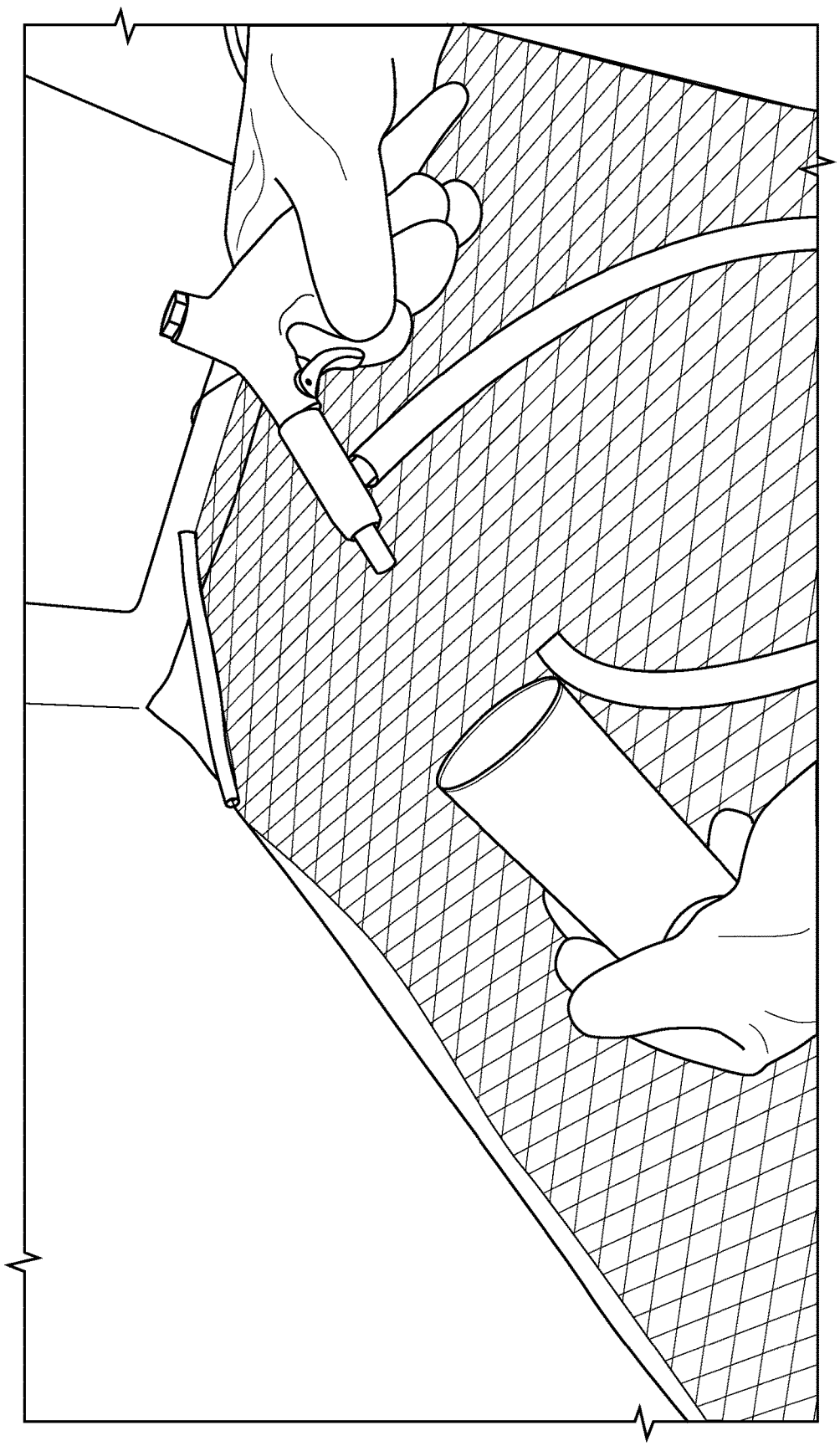
FIG. 8 shows nucleation sites being created inside a container, according to an exemplary embodiment of the present subject disclosure.

Various other glass and plastic containers may be treated by interior grit blasting and have demonstrated to behave in the same manner. Such a grit blasting process is shown in FIG. 8. Various beers and ales, including but not limited to Angry Orchard hard cider, Boulevard unfiltered wheat, single wide IPA, Tank 7 Farmhouse Ale, and Pale Ale; Budweiser, Carlsberg, Coors Banquet, Miller Lite, Guinness Draught, Heineken, Modelo Especial, Samuel Adams Boston Lager, Sapporo, Shiner Bock, Stella Artois, and TsingTao were shown to be quickly decarbonated using the nucleated containers.

Nucleation sites may be created on the container in a number of ways including, but not limited to: by use of a mold during manufacturing that contains a reverse image of the nucleation sites, by use of a container material that is naturally rough or naturally contains many nucleation sites, or by post treatment of the container after initial manufacturing using any number of well-known processes for creating a rough surface. These processes include: sandblasting, bead blasting, laser etching, acid etching, or other mechanical or chemical means for roughening the surface or creating nucleation sites.

Molding may also be used to create a rough surface, wherein the nucleation sites are produced during molding of the container, by using a mold containing a mirror image of the nucleation sites.

Sandblasting may be performed using aluminum oxide, silicon carbide, crushed glass, glass beads, plastic abrasive, pumice, steel shot, steel grit, corn cob, walnut shell or garnet with a grit ranging from 8 to 1,000. Laser etching may be performed with any number of commercially available laser cutter/etcher systems. Plastic containers, especially, may be manufactured with a multitude of nucleation sites by using a mold that has be roughened using sandblasting or other methods.

The nucleation sites may be created in any number of types of materials including, but not limited to: glass, ceramic, metal, plastic, thermoplastic, polytetrafluoroethylene or other material routinely used for producing bottles or sample tubes for laboratory use. The container may be autoclavable, such that it can be washed and then autoclaved between samples to ensure that no cross contamination occurs between samples. Alternatively, the container may be single use and may be packaged and treated, prior to sale, using e-beam irradiation, gamma irradiation, ethylene oxide, vaporous hydrogen peroxide, peracetic acid or other commonly used sterilization processes.

The container is sized such that entire sample may be vigorously poured into the container and not overflow due to the decarbonation process and associated foaming of the sample. In the case of beer, most sample 350 mL cans or bottles of beer can be rapidly poured into a container of 1 L nominal volume without overflowing during the decarbonation process. Other samples types and volumes may require larger containers or may be able to be processed in smaller containers.

Applicants have proven the effectiveness of the present technique with various volumes. For example, from 100 mL of beer to 750 mL of sparkling wine. Degassing of up to 12 ounces (335 mL) of beer has been performed in 32 ounce straight sided jars (like the jars shown in FIGS. 2 and 9). A 750 mL wine sample was degassed in a 60 ounce sand blasted beer pitcher and was run on the Concentrating Pipette with a 0.4 um Concentrating Pipette Tip in 12 minutes and 35 seconds. The present technique is effective for a wide range of volumes, from 5 mL to 10 L. Further, different shapes of containers may also be used to enhance the decarbonation process through increased turbulence associated with different container diameters and shapes.

A large surface area with nucleation sites may also be produced by using a multitude of devices such as glass beads or a single device or several devices with a large surface area of nucleation sites which are placed into the container prior to pouring the sample.

The decarbonation process causes significant quantities of gas to be released and as such the process to some extent helps maintain sterility due to an outflow of carbon dioxide from the container. Further this outflow requires that an open container or some type of vent be used during the decarbonation process. For example, a loose-fitting lid may be used to eliminate the chance of a user touching the container opening while also constricting the open area enough to ensure only an outflow of carbon dioxide takes place. Further, lids with an integral membrane filter of a small enough pore size to ensure sterility may also be used to allow for an outflow of gas while helping to reducing the chance of contamination.

In addition to the decarbonation action performed by use of a sample container with a large surface area of nucleation sites, other steps may be taken to enhance the rate and completeness of the decarbonation process. These include vigorous pouring of the beer into the container, heating of the sample prior to pouring into the container, stirring or shaking of the sample while in the container, as well as other methods for enhancing mixing and contact with the nucleation sites. Further, the ability to process the sample following decarbonation may also be enhanced by cooling the sample during or after the decarbonation process to increase the solubility of the remaining carbon dioxide in the sample and thus make it more difficult to come out of solution during subsequent filtration or concentration processes.

Vigorous pouring of beer samples or other carbonated or gassed samples may entail turning the sample container—in the case of beer the bottle or can—nearly or completely upside down from a height of a few inches to one foot or more in height above the nucleated container and letting the entire sample flow into the container.

Heating of the sample includes any temperature from room temperature to up to 37° C. or more to enhance the release of carbon dioxide. In the case of beer tests were performed by putting full, unopened cans or bottles of beer in a 37° C. incubator for 30 minutes before pouring into the container. This significantly enhanced the carbon dioxide removal and reduced the total time period required for decarbonation and sample processing on the Concentrating Pipette.

Further, in addition to beer, other sample types such as cider, sparkling wine, champagne, wine coolers, other alcoholic beverages, juice, lemonade, coffee, soft drink, coke, fizzy drink, fizzy juice, cool drink, cold drink, lolly water, pop, seltzer, soda, soda pop, fountain drink, ginger ale, ginger beer, tonic water, mineral water, or other carbonated beverages may also be decarbonated using this method. Additionally, other fluid samples containing carbon dioxide, nitrogen, nitrous oxide, oxygen or other soluble gases or mixtures of soluble gases may also be degassed using these methods.

The more complete the removal of carbon dioxide from the beer or carbonated beverage the more quickly and completely the sample may be processed on the Concentrating Pipette. Without decarbonation of beer samples, most beer fouls the Concentrating Pipette Tip and causes the instrument to shut down within seconds. Provided below in Table 1 through Table 7 are data for processing of a number of brands and styles of beer following decarbonation. Table 1 through Table 5 show varying volumes of beer processed and varying run times for different types of beers and different types of Concentrating Pipette Tips. Table 6 and Table 7 provide a comparison between beer samples at room temperature and beer samples heated at 37° C. prior to processing.

Membrane filtration and concentration of biological particles including beer spoilage organisms spiked into Coors beer was then demonstrated using the Concentrating Pipette equipped with 0.45 micron hollow fiber pipette tips, P/N CC 08018. The first three test runs (test runs 1-3) are shown with a prototype next generation instrument with 3.5 psi backpressure and demonstrate an average of 693X concentration of the organism in an average of 3.6 minutes (see Table 6). Test runs 4-6 used the current generation instrument (CP-150) and test runs 7-9 used the next generation instrument (CP SELECT) without backpressure, with the difference being that the next generation instrument has improved valves, foam control, software, etc.

Optimization of the grit blasting (nucleating) process (FIG. 8) was undertaken using a commercially available autoclavable culture vessel (32 oz wide mouth glass jar with HEPA-vent lid, P/N C607, Phyto Technology Laboratories, Mission, Kans. USA). The vented lid allows the gas to escape during decarbonation without building up pressure in the jar. Aluminum Oxide sandblasting media and other media were screened for the ability to create an optimum surface for beer decarbonation, including but not limited to 150 grit blasted for 8 minutes which was selected for production of decarbonation vessels for commercial sale. Other values and time ranges are also possible and within the purview of the present disclosure.

Figure 9:
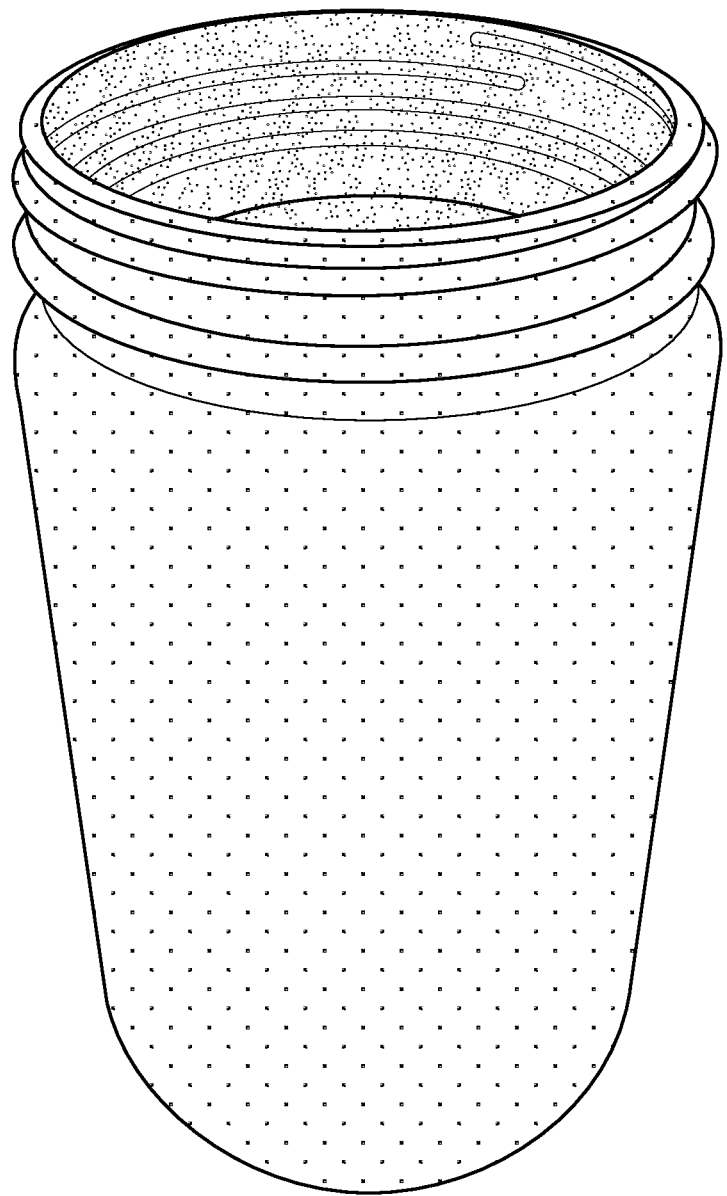
FIG. 9 shows an internally nucleated container, according to an exemplary embodiment of the present subject disclosure.

The blasting media size may range from 8-1,000 grit, and more specifically would be limited to 18-500 grit. Above 500 grit is the "micro fine" area and less conducive to creation of nucleation sites. Testing times have ranged from 1 minute (minimum to lightly blast the jar) to 32 minutes. The 32 minutes involved several instances of sandblasting with a fine grit blasting media. As such, the process was to blast, test, and repeat. Beyond 30 minutes is where effectiveness starts to drop. An exemplary preferable material used is 150 grit aluminum oxide for 6-8 minutes at ~100 psi. An internally nucleated jar is shown in FIG. 9.

In another exemplary embodiment, Styrofoam cups and containers are used. Styrofoam cups and containers inherently provide a vast number of nucleation sites due to their method of manufacture. Observation of such cups under a microscope clearly shows nucleation sites where cells border each other and where edges are created on the cells in the interstices between cells by injection into mold cavities.

Figure 10:
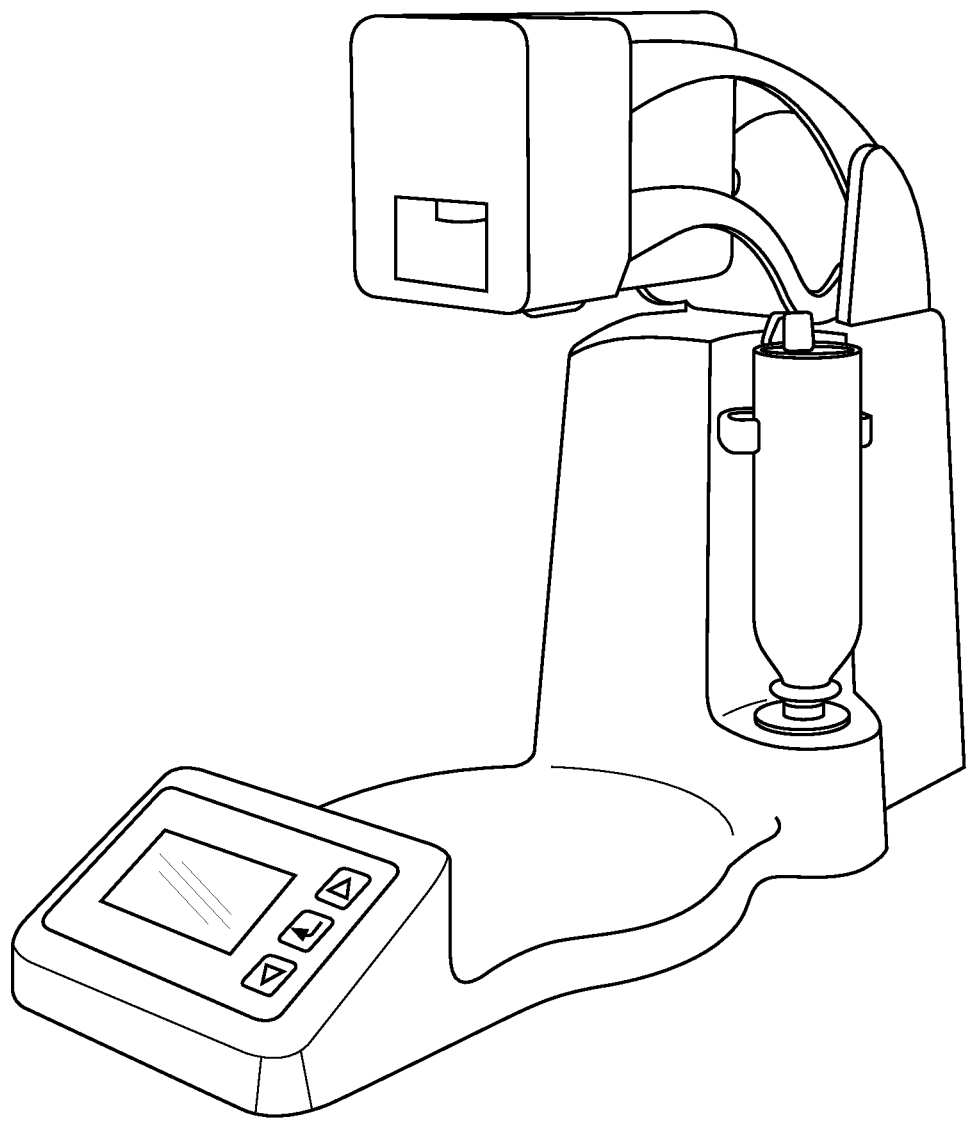
FIG. 10 shows a Concentrating Pipette Instrument, according to an exemplary embodiment of the present subject disclosure.

Three samples were degassed in Styrofoam cups and processed on the Concentrating Pipette Instrument (CP-150, FIG. 10). The appearance of the degassing process was similar to that in a frosted glass container. After pouring the beer in the cups, the standard lids with either the slit aperture for inserting a drinking straw, or the coffee drinking lid with the small sipping hole, were applied to the cups. Due to gas evolution from the cups, these small gas openings are sufficient to allow the evolving gas to escape without blowing the lids off. The evolving gas may also protect the sample from contamination during the settling and degassing step. In this case, the samples were chilled for an hour or less. See Table 9 for results of beer degassing using commercially available Styrofoam cups.

Following the above exemplary treatments, the Applicant Concentrating Pipette and other Applicant instruments based on the above patents and pending patent application Ser. Nos. 14/313,618, 15/456,981, 15/431,655, and 14/058,193 are able to concentrate the initial sample into a volume of from less than 100 to 1000 milliliters or more in a matter of minutes.

It will be appreciated that the foregoing instrumentalities teach by way of example, and not by limitation. Accordingly, those skilled in the art understand that the subject matter is not limited to what is strictly disclosed, but also pertains to what is understood by those skilled in the art on the basis of the teachings herein. The inventors hereby state their subject matter to rely, as may be needed, upon the Doctrine of Equivalents to protect the fullness of their rights in what is claimed.

TABLE 1

Concentration Pipette Run Times for Decarbonated Beer - Best Results (with 4° C. chilling)

| Beer | Tip | Volume processed | Average time (min) | Time at 4° C. (min) | Can/ bottle | Number of runs |
|---|---|---|---|---|---|---|
| Coors Banquet | 0.4 um flat | all (355 mL) | 13.86 | 20 (as low as 3) | both | 16 |
| Heinekin | 0.4 um flat | all (355 mL) | 17.26 | 20 | Bottle | 7 |
| Stella Artoise | 0.4 um flat | all (355 mL) | 8.82 | 20 | Bottle | 3 |
| TsingTao | 0.45 um hf-CPT | All (355 mL) | 8.7 | 20 | Bottle | 3 |

TABLE 2

Concentrating Pipette Run Times for Decarbonated Beer - 2nd Best Results (with 4° C. chilling)

| Beer | Tip | Average volume processed | Average time (min) | Time at 4° C. (min) | Can/bottle | Number of runs |
|---|---|---|---|---|---|---|
| Budweiser | 0.4 um flat | 265.33 mL | 22.74 | 20 | Can | 3 |
| Shiner Bock | 0.4 um flat | 259.9 mL | 34.13 | 20 | Bottle | 2 |
| Modelo Especial | 0.4 um flat | 167.67 mL | 10.96 | 20 | Can | 3 |
| Guinness Draught | 0.45 um hf-CPT | 170.11 | 16.74 | 20 | Both | 4 |
| Sapporo | 0.45 um hf-CPT | 238.99 | 17.5 | 20 | Can | 1 |

TABLE 3

Concentrating Pipette Run Times for Decarbonated Beer - 3rd Best Results (with 4° C. chilling)

| Beer | Tip | Avg volume processed (mL) | Average time (min) | Time at 4° C. (min) | Can/bottle | Number of runs |
|---|---|---|---|---|---|---|
| Boulevard Single Wide IPA | 0.4 um flat | 147.68 | 10.81 | 20 | Bottle | 4 |

TABLE 4

Concentrating Pipette Run Times for Decarbonated Beer - 4th Best Results (with 4° C. chilling)

| Beer | Tip | Avg volume processed (mL) | Average time (min) | Time at 4° C. (min) | Can/bottle | Number of runs |
|---|---|---|---|---|---|---|
| Samuel Adams Boston Lager | 0.4 um flat | 153.83 | 29.79 | 20 | Can | 2 |
| Angry Orchard had cider | 0.4 um flat | 127.70 | 31.44 | 20 | Bottle | 2 |
| Sapporo | 0.4 um flat | 127.27 | 19.33 | 20 | Can | 1 |
| Boulevard Pale Ale | 0.45 um hf-CPT | 147.68 | 11.1 | 20 | bottle | 2 |

TABLE 5

Concentrating Pipette Run Times for Decarbonated Beer - 5th Best Results (with 4° C. chilling)

| Beer | Tip | Average volume processed | Average time (min) | Time at 4° C. (min) | Can/bottle | Number of runs |
|---|---|---|---|---|---|---|
| Carlsberg | 0.4 um flat | 32.54 | 31.83 | 20 | Can | 2 |
| Boulevard Pale Ale | 0.4 um flat | 78.40 | 11.71 | 20 | Bottle | 2 |
| Boulevard Tank 7 | 0.4 um flat | 32.64 | 27.43 | 20 | Bottle | 1 |
| Boulevard Tank 7 | 0.45 um hf-CPT | 109.11 | 27.58 | 20 | Bottle | 1 |
| Boulevard unfiltered wheat | 0.45 um hf-CPT | 63.72 | 11.72 | 20 | Bottle | 1 |

TABLE 6

Concentration Pipette Run Times for Decarbonated Beer - Comparison −25° C. and 37° C. prior to decarbonation) (with 4° C. chilling)

| Beer | Temp prior to pouring | Average volume processed | Average time (min) | Tip type | Can/bottle | Number of runs |
|---|---|---|---|---|---|---|
| Coors Banquet | 25 | 355 | 13.86 | 0.4 um flat | Can | 16 |
| Coors Banquet | 37 | 355 | 6.53 | 0.4 um flat | Can | 3 |
| Budweiser | 25 | 255.33 | 22.74 | 0.4 um flat | Can | 3 |
| Budweiser | 37 | 452.76 | 16.51 | 0.4 um flat | Can | 3 |
| Heinekin | 25 | 354.1 | 17.26 | 0.4 um flat | Bottle | 7 |
| Heinekin | 37 | 349.82 | 10.8 | 0.4 um flat | Bottle | 1 |

TABLE 7

Concentration Pipette Run Times for Decarbonated Beer - Comparison −25 ° C. and 37° C. prior to decarbonation) (with 4° C. chilling)

| Beer | Temp prior to pouring | Average volume processed | Average time (min) | Tip type | Can/bottle | Number of runs |
|---|---|---|---|---|---|---|
| TsingTao | 25 | 119.74 | 20.91 | 0.4 um flat | Bottle | 3 |
| TsingTao | 37 | 131.98 | 6.27 | 0.4 um flat | Bottle | 1 |
| Stella Artois | 25 | 328.53 | 8.81 | 0.4 um flat | Bottle | 3 |
| Stella Artois | 37 | 324.96 | 6.22 | 0.4 um flat | Bottle | 1 |

TABLE 8

InnovaPrep Concentration of Beer Spoilage Organism from Decarbonated Beer
L. brevis spiked Miller High Life Mar. 14, 2017

| | 1 | 2 | 3 | avg | st dev | 4 | 5 | 6 |
|---|---|---|---|---|---|---|---|---|
| Runs | | | | | | | | |
| time | 3.00 | 4.00 | 3.82 | 3.6067 | 0.4352 | 6.70 | 4.82 | 4.17 |
| Feed Titer (~1 CFU/mL) plated 100 uL/counts | 196 187 164 | | | | | 196 187 164 | | |

TABLE 8-continued

InnovaPrep Concentration of Beer Spoilage Organism from Decarbonated Beer
*L. brevis* spiked Miller High Life Mar. 14, 2017

| | | | | | | | | |
|---|---|---|---|---|---|---|---|---|
| average | 182.3333 | | | | | 182.3333 | | |
| dilution | 1.0000 | | | | | 1.0000 | | |
| total spike | 182.3333 | | | | | 182.3333 | | |
| feed/titer, CFU/mL | 0.5136 | | | | | 0.5136 | | |
| Concentrate | | | | | | | | |
| tare | 3.7157 | 3.7149 | 3.69 | | | 3.7033 | 3.7036 | 3.7017 |
| net | 3.9074 | 4.0485 | 4.0881 | | | 4.3726 | 4.4142 | 4.5058 |
| volume | 0.1917 | 0.3336 | 0.3981 | 0.3078 | 0.0862 | 0.6693 | 0.7106 | 0.8041 |
| counts, CFUs | 93 | 99 | 114 | | | 106 | 105 | 102 |
| conctiter CFU/mL | 485.1330 | 296.7626 | 286.3602 | | | 158.3744 | 147.7625 | 126.8499 |
| % Efficiency | 51.01% | 54.30% | 62.52% | 55.94% | 4.84% | 58.14% | 57.59% | 55.94% |
| concentration factor for Extraction 2 | 944.5460 | 577.7919 | 557.5386 | 693.2922 | 177.8556 | 308.3524 | 287.6911 | 246.9747 |
| tare | 3.6966 | 3.7267 | 3.6951 | | | 3.6965 | 3.6936 | 3.716 |
| net | 3.9142 | 4.0673 | 3.9811 | | | 4.3905 | 4.4625 | 4.4615 |
| volume | 0.2176 | 0.3406 | 0.286 | 0.2814 | 0.0503 | 0.6940 | 0.7689 | 0.7455 |
| counts, CFU | 36 | 9 | 9 | | | 22 | 4 | 3 |
| Efficiency | 19.74% | 4.94% | 4.94% | 9.87% | 6.98% | 12.07% | 2.19% | 1.65% |
| total elution volume | 0.4093 | 0.6742 | 0.6841 | | | 1.3633 | 1.4795 | 1.5496 |
| total efficiency | 70.75% | 59.23% | 67.46% | 65.81% | 4.84% | 70.20% | 59.78% | 57.59% |

| | avg | st dev | 7 | 8 | 9 | avg | st dev |
|---|---|---|---|---|---|---|---|
| Runs | | | | | | | |
| time | 5.2300 | 1.0728 | 4.13 | 3.75 | 3.73 | 3.8700 | 0.1840 |
| Feed Titer (~1 CFU/mL) plated 100 uL/counts | | | 196 187 164 | | | | |
| average | | | 182.3333 | | | | |
| dilution | | | 1.0000 | | | | |
| total spike | | | 182.3333 | | | | |
| feed/titer, CFU/mL | | | 0.5136 | | | | |
| Concentrate | | | | | | | |
| tare | | | 3.7258 | 3.7249 | 3.688 | | |
| net | | | 4.1903 | 4.2205 | 4.0338 | | |
| volume | 0.7280 | 0.0564 | 0.4645 | 0.4956 | 0.3458 | 0.4353 | 0.0645 |
| counts, CFUs | | | 117 | 111 | 81 | | |
| conctiter CFU/mL | | | 251.8837 | 223.9709 | 234.2394 | | |
| % Efficiency | 57.22% | 0.93% | 64.17% | 60.88% | 44.42% | 56.49% | 8.64% |
| concentration factor for Extraction 2 | 281.0060 | 25.4993 | 490.4135 | 436.0677 | 456.0603 | 460.8472 | 22.4433 |
| tare | | | 3.6991 | 3.7065 | 3.6897 | | |
| net | | | 4.1750 | 4.1963 | 4.086 | | |
| volume | 0.7361 | 0.0313 | 0.4759 | 0.4898 | 0.3963 | 0.4540 | 0.0412 |
| counts, CFU | | | 10 | 6 | 2 | | |
| Efficiency | 5.30% | 4.79% | 5.48% | 3.29% | 1.10% | 3.29% | 1.79% |
| total elution volume | | | 0.9404 | 0.9854 | 0.7421 | | |
| total efficiency | 62.52% | 5.50% | 69.65% | 64.17% | 45.52% | 59.78% | 10.33% |

TABLE 9

Beer Degassing Using Commercially Available Styrofoam Cups

| Sample | Beer | Degassing Vessel | Chill time (min) | Processing Time (m:s) | Processed Sample (g) | 1st Elution (uL) |
|---|---|---|---|---|---|---|
| 1 | Miller High Life | 32 Oz. Styrofoam Cup (Dart 32AJ20) | 40 | 7:03 | 277 | 380 |
| 2 | Coors Banquet | 32 Oz. Styrofoam Cup (Dart 32AJ20) | 50 | 6:24 | 266 | 260 |
| 3 | Miller High Life | 12 Oz. Styrofoam (Sweetheart X12 67240) | 60 | 3:38 | 118 | 350 |

What is claimed is:

1. A system for degassing a fluid sample, the system comprising a container with a plurality of nucleation sites for exposing to the fluid sample, wherein a total area of the nucleation sites is at least 5% of a total surface area of contact of the fluid sample with the container, and wherein a lid with open holes or holes covered with a membrane filter material is used to allow gas to escape during degassing.

2. The system of claim 1, wherein the fluid sample contains carbon dioxide, nitrogen, nitrous oxide, oxygen or other soluble gases or mixtures of soluble gases.

3. The system of claim 1, wherein the fluid sample is one of a carbonated beverage, beer, cider, sparkling wine, champagne, wine cooler, alcoholic beverage, juice, lemonade, coffee, soft drink, coke, fizzy drink, fizzy juice, cool drink, cold drink, lolly water, pop, seltzer, soda, soda pop, fountain drink, ginger ale, ginger beer, tonic water, mineral water, or other carbonated beverage.

4. The system of claim 1, wherein the container is made from one of glass, Styrofoam, ceramic, metal, plastic, thermoplastic, polytetrafluoroethylene or other material routinely used for producing bottles or sample tubes for laboratory use.

5. The system of claim 1, wherein the nucleation sites are produced during molding of the container, by using a mold containing a mirror image of the nucleation sites.

6. The system of claim 1, where in the nucleation sites are produced after molding of the container by sandblasting, laser etching, machining, acid etching or other chemical or mechanical means of creating nucleation sites on the surface.

7. The system of claim 6, wherein the sandblasting is performed using aluminum oxide, silicon carbide, crushed glass, glass beads, plastic abrasive, pumice, steel shot, steel grit, corn cob, walnut shell or garnet with a grit ranging from 8 to 1,000.

8. A method for degassing a fluid, the method comprising:

pouring a fluid sample into a container with a plurality of nucleation sites, wherein a total area of the nucleation sites is at least 5% of a total surface area of contact of the fluid sample with the container and wherein a lid with open holes or holes covered with a membrane filter material is used to allow gas to escape during degassing; and incubating the fluid in the container for a sufficient time to allow for degassing.

9. The method of claim 8, wherein the fluid sample is poured into the container in such a manner to agitate the fluid sample and increase the rate of degassing.

10. The method of claim 8, wherein the fluid sample is first heated to increase the rate of degassing.

11. The method of claim 8, wherein the fluid is cooled during or after degassing to increase the solubility of the gas in the fluid.

12. A system for degassing a fluid sample, the system comprising a container with a plurality of nucleation sites for exposure to the fluid sample, wherein a total area of the nucleation sites is at least 5% of a total surface area of contact of the fluid sample with the container, wherein the nucleation sites are on a device or plurality of devices which are placed in the container, and wherein a lid with open holes or holes covered with a membrane filter material is used to allow gas to escape during degassing.

13. The system of claim 12, wherein the container is made from one of glass, Styrofoam, ceramic, metal, plastic, thermoplastic, polytetrafluoroethylene or other material routinely used for producing bottles or sample tubes for laboratory use.

14. The system of claim 12, where in the nucleation sites are produced during molding of the container, by using a mold containing a mirror image of the nucleation sites.

15. The system of claim 12, where in the nucleation sites are produced after molding of the container by sandblasting, laser etching, machining or other mechanical means of creating nucleation sites on the surface.

16. The system of claim 15, wherein the sandblasting is performed using aluminum oxide, silicon carbide, crushed glass, glass beads, plastic abrasive, pumice, steel shot, steel grit, corn cob, walnut shell or garnet with a grit ranging from 8 to 1,000.

17. The system of claim 12, wherein the container is of sufficient size to allow the fluid sample to foam while not overflowing the container.

* * * * *